United States Patent [19]

Caporale

[11] Patent Number: 5,767,238

[45] Date of Patent: Jun. 16, 1998

[54] INVERSE SOLID PHASE SYNTHESIS

[75] Inventor: Lynn H. Caporale, La Jolla, Calif.

[73] Assignee: CombiChem, Inc., San Diego, Calif.

[21] Appl. No.: 483,143

[22] Filed: Jun. 7, 1995

[51] Int. Cl.[6] .................. A61K 38/00; C07B 37/12
[52] U.S. Cl. ............ 530/334; 530/338; 530/339; 530/344; 588/361
[58] Field of Search ............... 530/336, 338, 530/339, 349

[56] References Cited

U.S. PATENT DOCUMENTS 5,288,514  2/1994  Ellman ................... 435/4

FOREIGN PATENT DOCUMENTS

WO93/09668  5/1993  WIPO.

OTHER PUBLICATIONS

WPIDS abstract 90–287857 (JP 02204474) 1990.
Bayer and Mutter, *Nature*, 237:512–513 (1972).
Bayer, et al., *J. Am. Chem. Soc.*, 96:7333–7336 (1974).
Bonora, et al., *Nucleic Acids Res.*, 18:3155–3159 (1990).
Bayer, et al., *Peptides: Chemistry, Structure, Biology*, 425–432.
Product Information for the Empore™ Disk.
Fodor et al., *Science*, 251:767–773 (1991).
Geysen, et al., *Proc. Natl. Acad. Sci. U.S.A.*, 81:3998–4001 (1987).
Frank and Doring, *Tetrahedron* 4:6031–6040 (1988).
Eritja, et al. *Tetrahedron* 47:4113–4120 (1991).
Maeji et al., *J. Immun. Methods* 146:83–90 (1992).
Haralambidis et al., *Nucleosides and Nucleotides* 10:333–337 (1991).
Juby, et al., *Tetrahedron Letters*, 32:879–882 (1991).
Houghton, et al., *Nature*, 354:84–86 (1991).
Cwirla, et al., *Proc. Natl. Acad. Sci. U.S.A.*, 87:6378–6382 (1990).
Leznoff, *Accounts of Chemical Research*, 11:327–333 (1978).
Xu, et al., *Can. J. Chem.*, 61:1405–1409 (1982).
Pittman and Smith, *J. Am. Chem. Soc.*, 97:1749 (1975).
Wang and Fox, *J. Org. Chem.*, 59:5358–5364 (1994).
Angeletti, et al., *Tetrahedron Letters*, 29:2261–2264 (1988).

*Primary Examiner*—Cecilia J. Tsang
*Assistant Examiner*—Michael Borin
*Attorney, Agent, or Firm*—Townsend and Townsend and Crew, LLP

[57] ABSTRACT

This invention relates to a method of inverse solid phase synthesis in which reactants are reacted in solution and a solid phase matrix is used to separate unreacted reactants from desired product.

11 Claims, 1 Drawing Sheet

INVERSE SOLID PHASE SYNTHESIS

FIELD OF THE INVENTION

The present invention relates to products and methods useful in solution chemistry.

BACKGROUND OF THE INVENTION

Interest in the synthesis of chemical compounds for use in basic research or drug discovery has led to the development of a number of methods for synthesizing organic compounds. In the chemical synthesis of organic compounds, two or more organic reactants are combined under appropriate conditions to give rise to a desired product which must be purified away from other products or unreacted reactants.

Methods for solid phase chemical synthesis have facilitated the separation of product from unreacted reactants. In solid phase synthesis, a reactant is first covalently linked to a solid support or matrix. A chemical reaction between the first reactant and a second reactant results in a product which is covalently linked to the solid support. If desired, additional reactants can be added to the product of the first reaction in subsequent reactions.

There are many advantages to solid phase synthesis over traditional synthesis methods in solution. Because the growing product is bound to the solid support, unreacted reactants can be easily removed by washing and/or filtration after each reaction in the synthesis of the final product. Furthermore, because of the ease of removal of unreacted reactants, the synthesis and separation of product from unreacted reactants can be automated. In addition, because unreacted reactant can be easily separated from the product, it is possible to use a large excess of reactants to try to drive the reaction to completion.

Several methods of solid phase chemical synthesis have been described for various biochemical compounds, including peptides, oligonucleotides, conjugates of peptides and oligonucleotides, and other organic compounds with diverse structures. Merrifield first described solid phase peptide synthesis in 1963. Merrifield, J. Am Chem. Soc. 85:2149–2154 (1963). Other methods of solid phase synthesis for peptides have been more recently described. See, e.g., Fodor, et al., Science 251:767–773 (1991); Lam, et al., Nature 354:82–86 (1991); Geysen, et al., Proc. Natl. Acad. Sci. USA 81:3998–4001 (1987) (synthesis of peptide sequences on "pins" corresponding to microtiter wells); Frank and Doring, Tetrahedron 44:6031–6040 (1988) (synthesis of peptides on different cellulose disks supported in a column).

In addition, methods for the synthesis of other organic compounds such as oligonucleotides, conjugates of oligonucleotides and peptides, and peptide-carrier conjugates have also been described. See, e.g., *Oligonucleotide Synthesis*, (M. J. Gait, editor), Oxford University Press 1990; Eritja, et al., Tetrahedron 47:4113–4120 (1991); Maeji, et al., J. Immun. Methods 146:83–90 (1992); Haralambidis, et al., Nucleosides and Nucleotides 10:333–337 (1991); Juby, et al., Tetrahedron Letters 32:879–882 (1991).

Recent interest in the preparation of large libraries of chemical compounds for use in screening assays has led to the development of a number of methods for the solid phase synthesis of molecular libraries having great diversity. In combinatorial chemistry, each reactant from a first group of reactants is reacted with each reactant from a second group of reactants to yield products containing all the combinations possible from the reaction. If desired, all of the products from the first reaction are then reacted with each reactant from a third group of reactants to yield a large array of products. Additional reactions, if desired, can further increase the size of the library of compounds.

Methods for solid phase synthesis of large combinatorial peptide libraries for use in basic research, drug discovery or identifying ligand-binding activity have been described. Geysen et al., Proc. Natl. Acad. Sci. 81:3998 (1984); Lam, et al., Nature 354:82–84 (1991); Houghten, et al., Nature 354:84–86 (1991), and WO 92/00091 (PCT/US91/04666); Cwirla, et al., Proc. Natl. Acad. Sci. USA 87:6378–6382 (1990).

In addition, Ellman, U.S. Pat. No. 5,288,514 describes the combinatorial synthesis of benzodiazepine compounds on a solid support. Ellman further discloses the use of a 96 pin block in which the pins act as a solid support for the sequential coupling of benzodiazepines. The pins of the 96 pin block are configured to be lowered into a series of 96-well microtiter reaction plates.

Winkler et al., WO93/09668 (PCT/US92/10183) discloses another method and device for the solid phase synthesis of a large library of polymers. The method and device relies on the use of thousands of channels to deliver compounds to a substrate on a surface to generate large arrays of polymers with diverse structures on the substrate surface.

Other uses of insoluble polymer supports in organic chemistry have also been described, including uses for reactants bound to insoluble polymers. For instance, Leznoff and co-workers have described the use of a blocking agent covalently bound to an insoluble polymer for blocking a symmetrical difunctional compound on only one of the two functional groups. Leznoff, Accounts of Chemical Research 11:327–333 (1978); Xu, et al. Can. J. Chem. 61:1405–1409 (1982). The monoblocked compound can easily be separated from an excess of unreacted difunctional compound by filtration or washing, thereby simplifying the purification of the monoblocked compound. Resins which contain catalysts for organic reactions have also been described. See, e.g., Pittman and Smith, J. Am Chem. Soc. 97:1749 (1975); Wang and Fox, J. Org. Chem. 59:5358–5364 (1994); Angeletti, et al. Tetrahedron Letters 29:2261–2264 (1988).

Methods for carrying out liquid phase synthesis of libraries of peptides and oliqonucleotides coupled to a soluble oligomeric support have also been described. Bayer, Ernst and Mutter, Manfred, Nature 237:512–513 (1972) ; Bayer, Ernst, et al., J. Am. Chem. Soc. 96:7333–7336 (1974); Bonora, Gian Maria, et al., Nucleic Acids Res. 18:3155–3159 (1990). Liquid phase synthesis methods have the advantage over solid phase synthesis methods in that liquid phase synthesis methods do not require a structure present on a first reactant which is suitable for attaching the reactant to the solid phase. Also, liquid phase synthesis methods do not require avoiding chemical conditions which may cleave the bond between the solid phase and the first reactant (or intermediate product). In addition, reactions in a homogeneous solution may give better yields and more complete reactions than those obtained in heterogeneous solid phase/liquid phase systems such as those present in solid phase synthesis.

In oligomer-supported liquid phase synthesis the growing product is attached to a large soluble polymeric group. The product from each step of the synthesis can then be separated from unreacted reactants based on the large difference in size between the relatively large polymer-attached product and the unreacted reactants. This permits reactions to take place in homogeneous solutions, as well as eliminating tedious purification steps associated with traditional liquid phase synthesis. Oligomer-supported liquid phase synthesis has also been adapted to automatic liquid phase synthesis of peptides. Bayer, Ernst, et al., Peptides: Chemistry, Structure, Biology, 426–432.

SUMMARY

This invention features methods and devices for carrying out inverse solid phase synthesis. This invention may be useful in the preparation of organic compounds, for instance, in the preparation of compounds containing the following functional groups: esters including aryl esters, amides including aryl amides, alicyclic compounds, carbocyclic compounds, heterocyclic compounds including furans, indoles, imidazoles, pyridines and pyridines, piperidines, pyrrolidines, guanidines, tetrazoles, benzazepines, benzodiazapene, β-lactams, and thienyl and pyrazinyl compounds, all optionally substituted; peptides having α-, β-, or ω-amino acids, oligonucleotides, oligosaccarides, phospholipids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, other polymers, or conjugates of two or more of the polymers listed above, or of two or more monomeric units which make up the polymers listed above. In addition, either the reactant or product, or both, may contain more than one functional group, which may be the same or different type of functional group.

More particularly, this invention is also useful in combinatorial chemistry, particularly automated combinatorial chemistry. By retaining the advantages of solid phase synthesis and liquid phase synthesis methods without the disadvantages of those methods, inverse solid phase synthesis facilitates the automation of traditional methods of liquid phase chemical synthesis.

The ability to automate inverse solid phase synthesis methods is especially useful when employed in the preparation of combinatorial libraries of compounds. Inverse solid phase synthesis methods can be used in the automatic synthesis of libraries of molecules with diverse structures for use in basic research or in screening protocols. The compounds of a library may contain a common scaffold group, or core molecule to which other functional groups are attached. A "scaffold" group is a chemical group which is common to all of the compounds in the library, and to which other functional groups have been added during synthesis of the library. The functional groups may be the same or different from each other. A "multifunctional scaffold" group is a scaffold group to which more than one functional group has been added. The compounds in the libraries can be screened for the discovery of pharmaceutical drugs or other useful chemicals, such as veterinary drugs, diagnostic reagents, pesticides, herbicides, novel materials, or compounds with other biological activities.

In inverse solid phase synthesis, chemical reactions occur in solution, while a solid phase is used to facilitate removal of excess unreacted reactant. A solid phase support may be used to remove either unreacted reactant or to collect the desired product following each step in the synthesis of a final product. In a variation of inverse solid phase synthesis, the solid phase may be used to bind a reactant or catalyst for introduction into the reaction mixture.

In a first aspect, this invention features a method of inverse solid phase synthesis in which a reactant is first reacted in solution to obtain a product. Following the reaction, unreacted reactant is removed with a solid phase support, while substantially all of the product is left in solution.

A reactant is any chemical which can undergo a chemical reaction to form a new bond. Because the reactants and the reaction conditions are not limited, inverse solid phase synthesis can be used with a very broad spectrum of chemical reactions, and is applicable to nearly all organic reactions.

The chemical synthesis will preferably involve two or more sequential reaction steps. A reaction step refers to one reaction in a series of reactions. Removal of unreacted reactants following each reaction step is preferably performed after each reaction, before proceeding to the next reaction step. One or more reactants may be incorporated into a growing product at each reaction step of the synthesis. The synthesis will preferably consist of 1–50 reaction steps. Preferably the synthesis will be automated.

An "automated" method of synthesis is one in which a self-operating device is used to deliver at least one of the reactants to more than one reaction vessel, and to simultaneously carry out parallel multiple reactions, each in a separate reaction vessel. Each of the reactants delivered may be the same or a different reactant. The "self-operating device" is one which does not require manual manipulation for the delivery of the reactant to each reaction vessel. Delivery is the physical transfer of a reactant from a container to the reaction vessel. Preferably the number of simultaneous reactions will be greater than 2 and less than 100. Even more preferably the number of simultaneous reactions will be eight or more reactions. In addition, two or more sets of simultaneous reactions can be carried out as part of one automated "reaction step" in a chemical synthesis of a library of compounds. The different sets of simultaneous reactions may have the same or a different starting time.

For descriptions of organic reactions well known to those in the art, see generally, March, J., *Advanced Organic Chemistry: Reactions, Mechanisms, and Structure*, (3d. ed. 1984); *Comprehensive Organic Synthesis*, (Barry M. Trost, editor-in-chief and Ian Fleming, deputy editor-in-chief) (1991). The bond formed by the chemical reaction can be any desired type of covalent or organometallic bond. Examples of such bonds including the following: carbon-carbon single bond, carbon-carbon double bond, organometallic, heterocyclic (where the heterocyclic product may be aromatic or saturated), peptide [$R^1CONHR^2$], ester [$R^1C(O)OR^2$], sulfonamide [$R^1SO^2NR^2$], thioester [$R^1C(O)SR^2$], phosphodiester [$R^1OP(O)R^2$], ether [$R^1COCR^2$], thioether [$R^1CSCR^2$], amide [$R^1C(O)N(R^2)R^3$], phosphamide [$R^1P(O)NH$—], amine [$R^1N(R^2)R^3$] and azo [—CNNC]] (where each $R^1$, $R^2$, and $R^3$ may be the same or different, cyclic or acyclic; may be, for example, hydrogen, alkyl, alkenyl, alkynyl, heterocyclic, or aryl; and may contain one or more functional groups). A chemical reaction does not include the formation of hydrogen bonds such as the hybridization of double-stranded DNA or the solubilization of a salt or compound in a liquid phase.

As used herein, the term "alkyl" refers to an aliphatic hydrocarbon group or compound, preferably a saturated hydrocarbon, either unbranched or branched. The alkyl group may be optionally substituted with one or more functional groups which are attached commonly to such chains, preferably hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, and the like. The alkyl group may be cyclic or acyclic. An alkane is a compound containing an alkyl group.

An "aryl" group is any aromatic group with a substituent group attached directly to a ring carbon.

The aryl group may be substituted with one or more functional groups which are attached commonly to such compounds, such as hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, sulfonyl, and the like.

The term "alkenyl" denotes an alkyl group as defined above having at least one double bond, such as, e.g., vinyl, allyl, 1-propenyl, isopropenyl, 1-butenyl, 2-butenyl, 3-butenyl, methallyl, or 1,1-dimethylallyl. An alkene is a compound containing an alkenyl group. The alkene may also contain two or more conjugated double bonds.

An "alkynyl" group refers to an unsaturated hydrocarbon group containing at least one carbon-carbon triple bond, including straight-chain, branched-chain, and cyclic groups. Preferably, the alkynyl group has 1 to 12 carbons. The alkynyl group may be substituted or unsubstituted. When substituted the substituted group(s) may be hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, sulfonyl, and the like.

The term "organometallic bond" refers to a bond between a carbon atom and a metal atom, and may be covalent or ionic depending on the structure of the carbon moiety, the nature of the metal ion, and the properties of the solvent. The term also includes a bond between a carbon atom and a metal atom which is difficult to characterize as exclusively covalent or ionic.

A "heterocyclic" group contains a ring made up of carbon atoms and at least one other type of atom, for example, nitrogen, oxygen, or sulfur. The heterocyclic product may be aromatic or saturated.

The term "alkoxyl" denotes the group —OR, where R is alkyl as defined above, such as methoxy, ethoxy, n-propoxy, iso-propoxy, n-butoxy, sec-butoxy, iso-butoxy, or tert-butoxy and the like.

A "cyclic molecule" is a molecule which has at least one chemical moiety which forms a ring. The ring may contain three atoms or more. The molecule may contain more than one cyclic moiety, the cyclic moieties may be the same or different.

An "acyclic" group does not contain a ring structure. However, the molecule may be straight or branched.

Preferably a reactant will be an organic chemical. Even more preferably, the reactant will be selected from natural or unnatural moieties including alkanes, alkenes, dienes, dienophiles, alkynes, aromatic compounds, heterocyclic compounds, ethers, amines, amides, esters, thioesters, compounds containing a carbon-hetero multiple bond, L-amino acids, D-amino acids, synthetic amino acids, nucleotides, sugars, lipids and carbohydrates.

A carbon-hetero multiple bond is a multiple bond between a carbon atom and a second type of atom. Examples of carbon-hetero multiple bonds are carbon-nitrogen double bonds, carbon-nitrogen triple bonds, carbon-sulfur double bonds, or carbon-oxygen double bonds. Examples of compounds containing carbon-oxygen double bonds are carboxylic acids, ketones, aldehydes, amides, esters, and thioesters.

A solid phase support is any macromolecular structure which is insoluble under the conditions for its use, and to which binding agents, reactants or catalysts can be attached, or which contains pores of a size to exclude desired product while permitting unreacted reactant to enter. The solid phase support may take different forms, have different physical characteristics, may be of different chemical compositions, and may be composed of a mixture of different chemical compositions, as long as the solid phase support is able to selectively retain unreacted reactants, desired product, or reactants or catalysts. The solid phase support should also be easily separated from the liquid phase, for instance, by trapping the solid phase support on the opposite side of a barrier containing openings of a size sufficient to completely block the flow of the solid support, while permitting the liquid phase and any soluble compounds in the liquid phase to readily pass through the openings. For example, the barrier may be a filter membrane. In another example, the pores of the barrier may be such that particles retained are those retained on a 140–400 standard sieve mesh, preferably, on a 200–400 standard sieve mesh.

The solid phase support may consist of a single component, such as a single surface which may be porous or non-porous, channeled, convoluted, uneven or smooth; or the solid phase support may consist of multiple components, such as the beads of a chromatographic resin or matrix, or silica beads. In addition, hollow fibers, with pore sizes that are permeable to excess reactant or product, also could be used for this solid phase extraction step.

The solid phase may be also be integrated into a structure which can be contacted with the reaction mixture and then removed. For instance, the hollow fibers themselves may be derivatized by a functional group that will bind to the excess reactant or product, or a second solid phase support bearing a binding agent may be held within the lumen of the fibers. In addition, the solid phase may be integrated into a particle-loaded membrane in which solid phase particles are immobilized within a stable, inert matrix.

Where binding agents, reactants or catalysts are attached to the solid phase support, the support may be porous, or non-porous. Where the solid phase support is used to remove unreacted reactant or to remove product, the degree of porosity will be chosen based on the binding capacity of the solid phase support, on the desired time for equilibration of interaction of the solid phase support with the reactant or product, and on the desired time for drainage and washing steps.

For instance, when the interaction between the retained compound and the solid support is not based on size exclusion, the use of a non-porous solid phase support will decrease the time required for binding and washing. However, if a non-porous solid support is used, the binding capacity of the outer surfaces of the components of the solid phase support must be sufficient to bind substantially all of the unreacted reactant or product in the desired time period.

Porosity refers to the total pore volume within the solid support. Porosity increases with increasing pore volume, which is determined by the number of pores and the size of each pore. The exclusion limit of a support is determined by the size of the largest molecule which can penetrate the pores under a given set of conditions. The porosity and exclusion size can be chosen by one skilled in the art to provide enough interaction sites to bind all of the unreacted reactant, desired product or reactant or catalyst, and to permit removal or separation within the preferred time, e.g., 2 hours or less. Preferably the removal or separation will take place in 1 hr. or less. In more preferred embodiments, the removal or separation will take place in 30 minutes or less, 15 minutes or less, or 5 minutes or less. In other preferred embodiments, the removal or separation will take place in 3 minutes or less, or 1 minute or less.

Generally the pores will be large enough under the given solvent conditions, at the temperature of the reaction to allow draining of all solvents used during synthesis steps within a time period of about one hour, more preferably 30 minutes or less, and even more preferably 10 minutes or less, 5 minutes or less, or 3 minutes or less.

Where use of a porous solid phase support is desired, the use of a solid phase support with a low degree of crosslinking may facilitate the diffusion of compounds into the polymer resin. However, where the solid phase support is used to remove excess reactant, it may also be preferable to chose a porous solid phase support with a higher exclusion limit in order to take advantage of separation based both on size exclusion and binding interactions.

Several solid supports useful for separation of product from unreacted reactants have been described in the chemical and biochemical literature, and any such support may be used as long as the solid support is insoluble under the conditions used in the binding steps (including temperature, and solvent composition), and is substantially chemically inert to the binding conditions used.

The material of the reaction vessels and barriers are substantially inert (do not react with), and are substantially insoluble, in the solvent being used in a reaction or separation step. Such solvents may include water, acids such as trifluoroacetic acid and anhydrous hydrogen fluoride, bases such as diisopropylehtylamine, and organic solvents such as acetone, benzene, toluene, xylene, ethyl acetate, dimethylsulfoxide, methylene chloride, chloroform, dimethyl acetamide, N-methyl pyrrolidone, dimethylformamide and the like. The material of the reaction vessels may differ during different reaction steps, and the material of the barrier may differ during different separation steps, depending on the solvent or solvents which the reaction vessel or barrier will contact during a given step or steps.

As used herein, a matrix is a three dimensional grid. A molecular matrix may be formed by the crosslinking of molecules to form a three dimensional molecular grid. For instance, the beads of a chromatographic polymeric resin will contain a matrix formed by the crosslinking of the polymer forming the resin.

In the context of a device for chemical synthesis, the term matrix may refer to the three dimensional organization of an array of reaction vessels.

A resin is a polysubunit insoluble support, generally made up of particles or beads. The subunits of the beads of the resin may have binding agents covalently attached. The beads may be porous or non-porous.

By "removing unreacted reactant" is meant separating unreacted reactant from the product through interaction of the unreacted reactant with the solid phase support. This interaction may involve, for example, binding with a binding agent attached to the solid phase support. The binding may be the result of interactions such as electrostatic interactions, hydrophobic interactions, hydrogen bonding, covalent bonding, π—π interactions or a combination thereof. In addition, the interaction may also involve physical inclusion of the unreacted reactant in the pores of the solid support, while desired product is excluded from the pores.

A binding agent binds the compound to be retained (i.e., reactant, catalyst, excess reactant, or desired product) selectively, and preferably with high affinity.

Selectively means that a binding agent binds to the compound to be removed from the liquid phase, but does not significantly bind to compounds which are to remain in the liquid phase. Preferably the ratio of molecules of the compound to be removed from the liquid phase which are actually bound to the ratio of molecules to remain in the liquid phase which are actually bound is greater than 10:1. Even more preferably the ratio will be greater than 100:1. In addition, preferably the binding agent intended to bind unreacted reactant binds less than 30% of the desired product under the conditions employed. In other embodiments, the binding agent binds less than 20%, 10%, 5% or 1% of the desired product.

High affinity is affinity sufficient to permit binding of the compound to be removed from the liquid phase within the preferred time such that the amount of unreacted reactant which is not removed from the desired product will not substantially interfere with the next step of synthesis or purification. In order to avoid substantial interference with the next step of synthesis or purification the ratio of the desired product to unreacted reactant following the separation step will preferably be greater than 2:1, and even more preferably greater than 5:1. In still more preferred embodiments, this ratio will be greater than 10:1, or even more preferably 100:1, or 1000:1. The binding constant of the binding agent for the compound to be removed from solution will preferably be greater than $10^{-1}$.

The solid phase support is also preferably contained within an insoluble porous barrier, or retained on one side of an insoluble porous barrier, in order to facilitate removal of the solid phase support from the liquid phase. The insoluble barrier has pores of a size which allow the solution to freely pass, but which fully block the flow of the solid phase support.

After equilibration of the interaction between the unreacted reactant with the solid phase support, the solid phase support retaining unreacted reactant is then physically separated from the liquid phase. This is generally carried out by containing the solid phase support and liquid phase on opposite sides of the barrier. This is preferably done by raising the barrier above the level of the liquid phase solution, with the solid phase support above the barrier. The solid phase support is then drained, blown, and/or rinsed, in order to recover any liquid phase from the solid phase support. Another preferred procedure is to pump liquid through the solid phase, and then through the barrier, while the solid phase is retained by the barrier.

The barrier may take different forms, have different physical characteristics, may be of different chemical compositions, and may be composed of a mixture of different chemical compositions, as long as the barrier is able to prevent movement of the solid phase support across it and to permit the flow of the liquid phase. It is not necessary for the barrier to be uniformly porous, as long as the porosity is sufficient to permit recovery of the liquid phase within the desired time. For instance, where the barrier takes the form of a cap for a reaction vessel, it would be possible for only the bottom surface of the cap (the surface which will contact the liquid phase) to be porous, provided that the barrier can still function as desired.

The barrier can be made of any material with pores of a sufficiently small size to fully block the flow of the resin or matrix used with it, but large enough to permit the free flow of reactants and products through the pores. The size of the pores will vary depending upon the size of the solid phase support or its components. For instance, where the solid support is a resin, the pores must be small enough to prevent the flow of the resin beads. In addition, the composition of the barrier must be such that its ability to block the flow of matrix or resin will not be compromised by the solvents used. The barrier may be, for example, a frit, such as frits used in chromotagraphy. Examples of materials which meet the requirements include sintered glass or alternate glasses, teflon, and Kel-F, stainless steel, ceramics, metals, or plastics.

A second aspect of this invention features a method of inverse solid phase synthesis in which a reactant is reacted in solution to obtain a product, and substantially all of the product is removed with a solid phase support. This embodiment of the invention is also useful in the automated synthesis of combinatorial libraries.

"Substantially all of the product" preferably refers to at least 80% of the product. Even more preferably, it refers to at least 90% of the product. Still more preferably, substantially all of the product refers to at least 95% of the product.

By "removing substantially all of the product" is meant separating the product from unreacted reactant through interaction of the product with the solid phase. This interaction may involve, for example, binding of the product to a binding agent attached to the solid phase. The binding may be the result of interactions such as covalent bonding, electrostatic interactions, hydrophobic interactions, hydrogen bonding, π—π interactions, or a combination thereof.

Once the product has been bound by the solid phase support, the solid phase support can be separated from the liquid phase, and the product can be recovered by altering solvent conditions, or by varying the temperature or the pressure in the reaction vessel to weaken the interactions between the product and the solid phase support.

As above, preferably the chemical synthesis will involve two or more reaction steps. Also, removal of the product of each step is preferably performed after each reaction step.

In a third aspect of this invention, a reactant or catalyst can be non-covalently bound to a solid phase support. The solid support bearing the reactant or catalyst can then be introduced to the liquid phase to facilitate a specific coupling step; when the reaction is over, the solid phase support can be easily removed. This embodiment of the invention is also particularly useful in the automated synthesis of combinatorial libraries of compounds.

Preferably a catalyst will be bound to the solid phase support. The catalyst may be either enzymatic or non-enzymatic. Non-enzymatic catalysts may include, e.g., metal catalysts, coordination complexes of metal catalysts, or amine catalysts. Enzymatic catalysts may include, e.g., acyl transferases, cyclases, synthases, aldolases, nucleotide polymerases, antibodies with catalytic function, or other enzymes which mediate condensation reactions between monomeric compounds.

The reactant or catalyst may be bound or entrapped in the solid phase support by means of any desired type of bond, i.e., covalent, ionic, or coordination bonds.

Contacting means bringing the solid phase support into sufficient physical proximity with a reactant in a homogeneous liquid phase, such that the catalyst or second reactant bound to the solid support can interact with the reactant in the liquid phase. Contact between the solid phase bound reactant or catalyst and the reactant in solution preferably occurs after the liquid phase has passed through a porous insoluble barrier. Prior to the reaction, the solid phase support will be located on the opposite side of the barrier from the liquid phase.

Removing the solid support to which the reactant or catalyst is bound means separating the solid phase support from the liquid phase.

Other aspects of the invention make use of the featured methods used in a device for automated synthesis of combinatorial libraries.

There are many advantages to inverse solid phase synthesis. For instance, when the solid phase support is used to separate product from unreacted reactant, inverse solid phase synthesis eliminates the requirement for a covalent bond between a reactant and either an insoluble solid support or a soluble polymer support, which are required in solid phase synthesis or polymer-linked liquid phase synthesis, respectively. By eliminating this covalent bond and the need for the presence of a functional group to form this covalent bond, inverse solid phase synthesis permits the use of a wider range of conditions than in solid phase synthesis or polymer-linked liquid phase synthesis. Inverse solid phase synthesis therefore permits the use of conditions, including reaction and washing solvents, reactants, protecting groups, and coupling methods which might cleave such a covalent bond. These advantages facilitate the automation of combinatorial libraries.

Other advantages result from carrying out the reactions in a solution, in the absence of a large polymer. For instance, because inverse solid phase synthesis does not require attachment of a first reactant to a large polymer during the chemical reaction, there will be less steric hindrance during the reaction. In addition, reaction in a homogeneous solution can give rise to broader range of products compared with methods of solid phase synthesis. Also, because inverse solid phase synthesis facilitates the removal of excess reactants, a large excess of reactants can be used in reactions carried out using inverse solid phase synthesis. Solid phase synthesis methods thereby retain this advantage of traditional solid phase synthesis methods.

Still another advantage of inverse solid phase synthesis is the ease of scaling up a reaction which takes place in a homogeneous liquid phase.

Inverse solid phase synthesis also facilitates separation of the desired product from failure products which failed to react at critical steps of the synthesis. In addition, when the product is in the liquid phase, the completeness of the reaction can be monitored by taking aliquot volumes and analyzing the aliquots, e.g., by nuclear magnetic resonance, or by non-destructive spectrophotometric methods.

In addition, inverse solid phase synthesis eliminates the potential need to introduce a functional group onto the reactant in order to form a reaction- insensitive linker to the solid support or the soluble polymer.

Inverse solid phase synthesis also retains the ease of automation of solid phase synthesis or soluble polymer liquid phase synthesis.

Other and further objects, features and advantages will be apparent from the following description of the presently preferred embodiments of the invention.

DETAILED DESCRIPTION OF THE INVENTION

Figure 1:
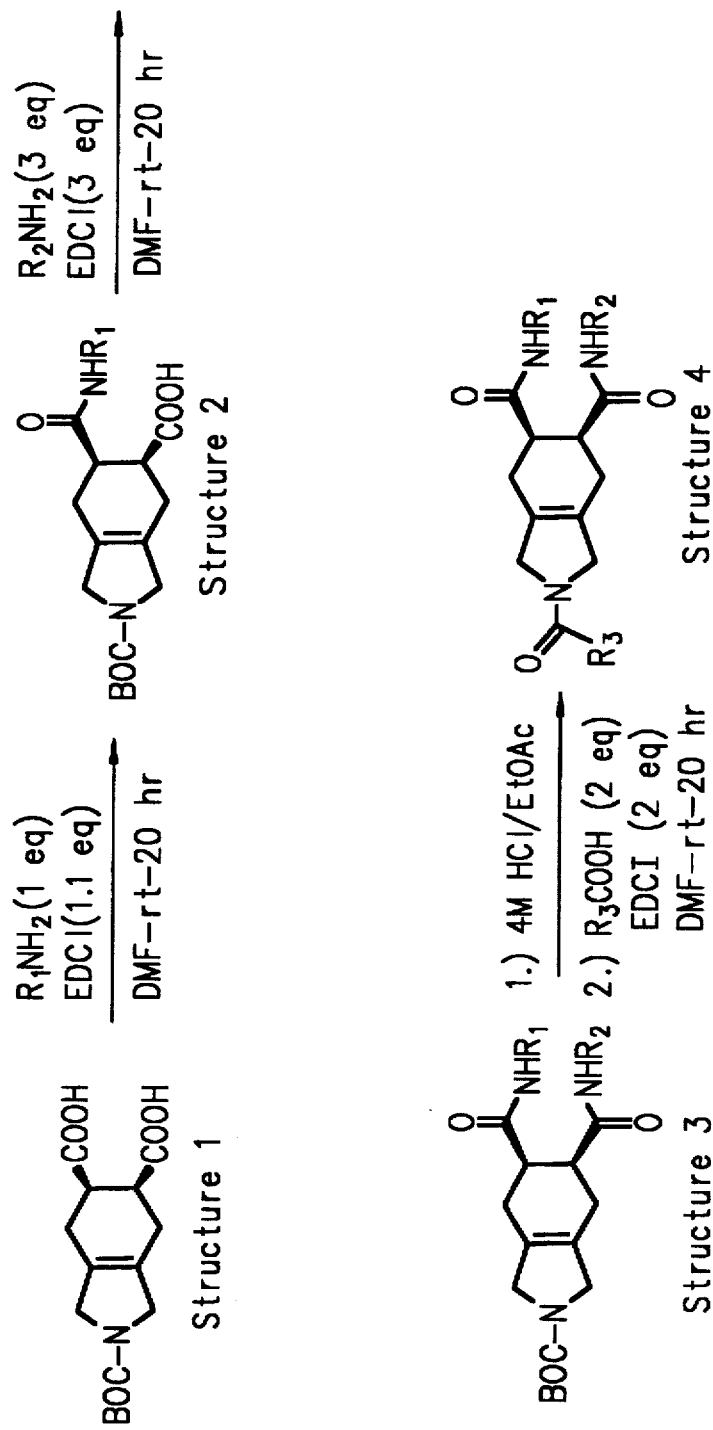
FIG. 1 shows a reaction scheme which can be used in the generation of a multifunctional scaffold molecule.

This invention relates to methods and devices for the chemical synthesis of organic compounds using inverse solid phase synthesis. Inverse solid phase synthesis is particularly useful in separating unreacted reactants or catalysts from the desired product in liquid phase chemical reactions. The methods of this invention utilize solid phase supports which can bind unreacted reactants, products, reactants or catalysts, and which are easily separated from a liquid phase.

Inverse solid phase synthesis is also useful for adapting for use in automated chemical synthesis. Preferably, inverse solid phase synthesis is used in a device for automated synthesis of combinatorial libraries of diverse chemical compounds. One such device is described in Brenner, U.S. patent application Ser. No. 08/281,194 filed Jul. 26, 1994, hereby incorporated by reference.

In addition, a variation of inverse solid phase synthesis is useful for introducing a solid phase bound reactant or solid phase bound catalyst into a liquid phase solution containing at least one liquid phase reactant. Where a catalyst is bound to the solid phase support, the liquid phase will preferably contain at least two organic reactants, preferably two organic reactants. Where a reactant is bound to the solid phase support, the liquid phase will preferably contain one reactant.

A. Use of a Solid Phase Support to Remove Reactants

Two or more reactants in a liquid phase are reacted in a reaction vessel. Preferably the reaction will be a condensation reaction between two organic reactants. The reactions to combine reactants will preferably include reactions proceeding through a carbocation, carbanion, free radical, carbene or nitrene intermediate (see, March, supra, at Chapter 5), photochemical reactions (see March, supra, at Chapter 7), reactions catalyzed by acids or bases (see March, supra, at Chapter 8), aliphatic nucleophilic substitutions (see March, supra, at Chapter 10), aromatic electrophilic substitutions (see March, supra, at Chapter 11), aliphatic electrophilic substitutions (see March, supra, at Chapter 12), aromatic nucleophilic substitutions (see March, supra, at Chapter 13), additions to carbon-carbon multiple bonds (see March, supra, at Chapter 15), additions to carbon-hetero multiple bonds (see March, supra, at Chapter 16), elimination reactions (see March, supra, at Chapter 17), rearrangements (see March, supra, at Chapter 18), and oxidation-reduction reactions (see March, supra, at Chapter 19).

A carbocation is a compound which contains a carbon atom which lacks a pair of electrons.

A carbanion is a compound which contains a carbon atom with an unshared pair of electrons.

A free radical is a compound which contains one or more unpaired electrons.

A carbene is a compound which contains a carbon atom with two nonbonded electrons which may be either paired or unpaired. A nitrene is a compound which contains a nitrogen atom with two nonbonded electrons which may be either paired or unpaired.

An aliphatic nucleophilic substitition is one in which a nucleophile brings an electron pair to the substrate, which it uses to form a new bond, and a leaving group departs with an electron pair. A nucleophile is an electron rich compound, and may be charged or uncharged. The leaving group may be charged or uncharged.

An aromatic electrophilic substitution reaction is one in which a positive ion or the positive end of a dipole or induced dipole attacks an aromatic ring and a leaving group departs without its electron pair. An electrophile is a compound which is deficient in electrons and is seeking electrons.

An aliphatic electrophilic substitution is one in which a positive ion or the positive end of a dipole or induced dipole attacks an aliphatic compound. This may result, for example, in the departure of a leaving group without its electron pair; cleavage of the substrate to form a carbonyl, decarboxylation of an aliphatic acid.

An aromatic nucleophilic substitution is a reaction in which a nucleophile reacts with an aromatic ring.

Addition reactions to carbon-carbon multiple bonds preferably include electrophilic additions. The electrophile may be a positive ion or the end of a dipole or an induced dipole.

Addition reactions to carbon-hetero multiple bonds may include electrophilic additions or nucleophilic additions, and may be catalyzed by either acids or bases.

Elimination reactions are reactions in which two groups are lost. Elimination reactions may result, for example, in the formation of a double bond from a single bond or a triple bond from a double bond ($\beta$-eliminations); the formation of a carbene or a nitrene ($\beta$-eliminations); or the formation of a three-membered ring ($\gamma$-eliminations). For example, dehydration of an alcohol by treatment with bromoform may give rise to an alkene product (see March, supra, at p. 903).

In rearrangements, one group moves from one atom to another atom in the same molecule. Rearrangements may include, for example, electrophilic rearrangments or nucleophilic rearrangements which proceed through the formation of a carbocation or nitrene.

The reactions may more preferably include the Diels-alder reaction for cycloaddition reactions between a conjugated diene and an $\alpha,\beta$-unsaturated carbonyl compound to form a six-membered ring (see *Comprehensive Organic Synthesis*, supra, Volume 5 at sections 4.1 to 4.5); the Heck reaction for the addition of an organomercurial compound to an alkene (see *Comprehensive Organic Synthesis*, supra, Volume 4 at pages 903–906); Wagner-Meerwein rearrangements of an alcohol after treatment with an acid (see *Comprehensive Organic Synthesis*, supra, Volume 3 at section 3.1; March, supra, at pp. 958–959); Wittig and Still rearrangements (see *Comprehensive Organic Synthesis*, supra, Volume 3 at pp. 979–984); and alkene-alkene coupling reactions, including Suzuki couplings (see *Comprehensive Organic Synthesis*, supra, Volume 4, at pp. 489–90).

A "diene" is a compound which contains at least two multiple bonds and reacts with the dienophile to form a Diels-Alder reaction product. The diene may be linear or cyclic. The simplest diene which could participate in the Diels-Alder reaction is 1,3 butadiene. The diene may contain one or more of any different number of chemical groups so long as the Diels-Alder reaction between the diene and dienophile still occurs. Such compatibility of chemical groups with the Diels-Alder reaction may be tested for by those of ordinary skill in the art.

A "Dienophile" is a compound containing a multiple bond, for example, a double or triple bond which reacts with a diene. The dienophile may be identical in structure to a diene with which it is reacted. The dienophile may be linear or cyclic. The simplest dienophile which may participate in the Diels-Alder reaction is ehylene. The dienophile may contain an electron-withdrawing group such as a carbonyl, cyano or nitro group conjugated with the multiple bond. The dienophile may contain one or more of any different number of chemical groups so long as the Diels-Alder reaction between the diene and the dienophile still occurs. Such compatibility of chemical groups with the Diels-Alder reaction may be tested for by those of ordinary skill in the art.

Following the reaction, the reaction mixture is contacted with a solid phase support which can retain the excess reactant. Preferably this contact takes place simultaneously in many wells. The solid phase support will preferably contain a binding agent for the excess reactant. Excess reactant is allowed to bind to the solid phase support, and the solid phase support containing the bound excess reactant is separated from the liquid phase by retaining the solid phase on the other side of a barrier.

In one preferred embodiment, the solid phase support is contained within a porous barrier. After introduction of the solid phase support into the reaction vessel, separation takes place by raising the porous barrier, with the solid phase support above the porous barrier. The solid support is then held in place above the level of the liquid phase. Solvent containing unbound product is recovered by draining, blowing or rinsing. In one such embodiment, the solid-phase support is attached to a set of caps designed to be inserted into the top of the reaction vessels. After binding of the unreacted reactant, this cap can be removed, and the liquid phase recovered as described above.

In another preferred embodiment, particularly useful in the COMBISYN® matrix device, the reaction mixture is transferred to a work station at which the reaction mixture is contacted with the solid phase, which binds unreacted reactants. Transfer may take place, for example, by pumping the reaction mixture from the reaction vessel to the work station, or by automated or manual movement of the reaction vessel to the work station. The liquid phase is then pumped through a barrier which retains the solid phase, and the liquid phase containing unbound product can be recovered. After the recovery step, the liquid phase can then be returned to the reaction vessel.

During this recovery step, a solvent appropriate for the next step of synthesis may be introduced into the reaction vessel, by washing the solid phase support with the appropriate solvent. If the recovery step has increased the volume of the liquid phase, or if it is otherwise desired to reduce the volume of the liquid phase, the volume of the liquid phase can be reduced with, e.g., evaporative methods such as drying under a stream of air or N2.

The reaction vessel is then made ready for the next step of synthesis.

B. Use of a Solid Phase Support to Retain Desired Product

In another embodiment, following the chemical reaction, a solid phase support containing a binding agent for the desired product is contacted with the reaction mixture. Desired product is allowed to bind until binding of the desired product has taken place, generally for 5 minutes to 2 hours, preferably for 30 minutes or less. The solid phase support containing the reversibly bound product can be retained in the reaction vessel or at the workup station, and washed extensively to remove excess reactant and/or to exchange the solvent. An appropriate solvent for the next synthesis step may be introduced during this washing step. Following completion of the desired washing steps, the bound product is released from the solid phase support by washing or contacting the solid phase support with an appropriate solvent which will eliminate or sufficiently decrease the interaction of the product with the solid phase support. The reaction vessel or workup station can be then be prepared for the next step.

If the recovery step has increased the volume of the liquid phase, or if it is otherwise desired to reduce the volume of the liquid phase, the volume of the liquid phase can be reduced with, e.g., evaporative methods such as drying under a stream of air or N2.

Preferably the solid-phase support is contained in a set of caps designed for introduction into reaction vessels. This set of caps can then be removed.

In another preferred embodiment, the reaction mixture is transferred from the reaction vessel to a work station at which the reaction mixture is contacted with the solid phase, which binds the desired product. Transfer can be carried out by pumping the reaction mixture from the reaction vessel to the work station or by manual or automated movement of the reaction vessels to the work station. The liquid phase is then pumped through a barrier which retains the solid phase, and the solid phase is washed with an appropriate solvent which will release the desired product. After the recovery step, the liquid phase can then be returned to the reaction vessel.

C. Screening for a Solid Phase Support with Appropriate Selectivity and Affinity.

1. Solid Phase Supports to Remove Excess Reactant

Appropriate solid phase supports may be commercially available from various sources, including Biorad, Pharmacia Fine Chemicals (Uppsala, Sweden; Piscataway, N.J.), Sigma Chemical Company (St. Louis, Mo.), 3M (St. Paul, Minn.). For example, if the excess reactant is an anion, an anion exchange resin can be used to bind the excess reactant. The anion exchange resin can be introduced by the method of this invention on one side of a barrier that is permeable to the reactants but not to the anion exchange resin. Examples of anion exchange resins include AG-1 and AG MP-1 resins, which bear the functional group R—$CH_2N^+(CH_3)_3$, AG-2 resins, which bear the functional group R—$CH_2(CH_2H_4OH)$ $N^+(CH_3)_3$ and AG-4 resins, which bear the functional group R—$CH_2N^+H(CH_3)_2$ on an acrylic matrix, AG-3 resins, which bear the functional group R—$CH_2N+H(CH_3)_2$. "BIOREX" 5 resin, which bears the functional groups R—$N^+H(CH_3)_3$ and R—$N^+(CH_3)_2C_2H_4OH$, resins which bear the functional group diethylaminoethyl (DEAE), and resins which bear the quaternary ammonium group $N^+(CH_3)_3$(Q). Still another example is the EMPORE™ extraction disk containing a quaternary ammonium functional group.

An excess reactant which is a cation can be bound and removed by the use of a cation exchange resin introduced by the method of this invention on one side of a barrier that is permeable to the reactants but not to the cation exchange resin. Examples of cation exchange resins include S, AG50W and AG-MP 50 resins, bearing the functional group R—$SO_3^-$, and "BIOREX" 70 and CM resins, which bear the functional group R—$COO^-$, the EMPORE™ cation exchange disk (containing a sulfonic acid functional group), and chelating resins which can remove polyvalent cations with high selectivity. An example of a chelating resin is "CHELEX" 100, which contains the functional group R—$CH_2N$ $(CH_2COO^-)_2$ If it is desired to remove both cations and anions from the product of a reaction (e.g., "desalt" a product), a resin containing both anionic and cationic functional groups can be used. Examples of such resins include mixed bed type resins such as "AG501-X8" and "BIOREX" MSZ 501 type resins, which contain both R—$SO_3^-$, and R—$CH_2N^+(CH_3)_3$ groups. A resin bearing weaker cations and anions, such as the "ion retardation" resin AG11A8 can be used to "desalt" even products containing anions and cations due to the differential affinity of salts and weaker anions to such a resin, as is used by one skilled in the art.

It may be possible to select a resin with sufficient crosslinking to exclude the product while permitting one or more reactants to enter the pores of the resin and be retained. For example, AG50W resins of various degrees of crosslinking may be selected which exclude molecules with a molecular weight greater than 400 (12% crosslinking), 1,000 (8%), 1,400 (4%), or 2,700 (2%). An example of a cation exchange matrix which can be obtained with various degrees of crosslinking is AG 1, which can be obtained to exclude molecules with a molecular weight greater than 1,000 (8% crosslinking), 1,400 (4%), or 2,700 (2%).

Other materials, commonly used in chromatography, can be introduced into the reaction vessel in order to separate product from excess reactants. For example, conditions can be adjusted by one skilled in the art so that a resin used in reverse phase chromatography can bind product or reactant to separate product from excess reactant. In addition, adjustment of the conditions by those skilled in the art can allow selective binding of less polar or more polar compounds by the use of normal phase chromatography on, for example, silica.

In addition, an affinity matrix that binds specifically to the product or excess reactant may be used. Examples of available affinity matrices include resins containing organomercurial groups that bind to thiol groups, or matrices bearing boronate residues which adsorb compounds containing groups such as cis-hydroxyl groups.

Certain activated supports are also useful for quenching excess unreacted reactant. For example, supports containing N-hydroxysuccinimide groups can remove primary amines by formation of covalent bonds. Other examples include matrices bearing hydrazide which can form a covalent bond with aldehyde or ketone groups, including carbohydrates. In addition, compounds containing carboxyl groups can be removed by the use of a resin bearing activated amino groups. Amino groups can be activated, e.g., by the use of a carbodiimide. Also, compounds containing amino groups can be removed by the use of a resin bearing activated carboxyl groups; carboxyl groups can be activated, e.c., by the use of a carbodiimide. Examples of carbodiimides include dicyclohexyl-carbodiimide, and 1-ethyl-3-(3-dimethylaminoproply) carbodiimide.

2. Solid Phase Supports to Bind Product

Anionic product can be bound to a solid phase support in order to remove nonanionic or less anionic excess reactant and by products. An anion exchange solid phase support can be introduced by the method of this invention on one side of a barrier that is permeable to the reactants but not to the anion exchange resin. Appropriate alterations of conditions by those skilled in the art can release the desired product from the solid phase support, and the product can be used in another reaction, if desired. For instance, one can use anion exchange resins such as AG-1 and AG MP-1 resins, which bear the functional group R—$CH_2N^+(CH_3)_3$, AG-2 resins, which bear the functional group R—$CH_2(CH_2H_4OH)N^+(CH_3)_3$, AG-4 resins, which bear the functional group R—$CH_2N^+H(CH_3)_2$ on an acrylic matrix, AG-3 resins, which bear the functional group R—$CH_2N^+H(CH_3)_2$, "BIOREX " 5 resin, which bears the functional groups R—$N^+H(CH_3)_3$ and R—$N^+(CH_3)_2C_2H_4OH$, resins which bear the functional group diethylaminoethyl (DEAE), and resins which bear the quaternary ammonium group $N^+(CH_3)_3$ (Q) resins.

If the product is a cation, a cation exchange solid phase support can be used to bind the product until noncationic or less noncationic excess reactant and byproducts are removed. The cation exchange resin can be introduced into the reaction vessel by the method of this invention on one side of a barrier that is permeable to the reactants but not to the cation exchange resin. Appropriate alteration of conditions by those skilled in the art can release the desired product from the matrix for use in another synthesis step, if desired. Examples of cation exchange resins include S, AG50W and AG-MP 50 resins, bearing the functional group R—$SO_3^-$, and "BIOREX " 70 and CM resins, which bear the functional group R—$COO^-$.

If an appropriate matrix is unavailable commercially, such a matrix can be made by one skilled in the art by attaching a substance known to bind to the product or reactant much as the sulfhydryl-binding resin was designed. If an appropriate ligand is not known, combinatorial methods can be used to synthesize and to screen and counterscreen to identify a matrix that will bind selectively and with high affinity to the excess reactant under the solvent conditions present at that step of the synthesis. For example, screening methods can be designed by one skilled in the art to identify a matrix component that will bind selectively to a broad range of compounds bearing a functional group which is contained in a family of reactants used in a given combinatorial chemistry synthesis step, but which is altered during the course of the reaction and thus lacking in the product.

Similarly, a solid phase support can be identified, or discovered via combinatorial synthesis and screening, that binds selectively, with high affinity, and reversibly, to a desired product or intermediate. Such a matrix could be discovered, for example, by screening against a broad range of compounds containing a structure that is introduced during the reaction step and is therefore lacking from the starting materials.

In addition, the use of smaller particles may allow faster separation of materials if the machine can operate under sufficient pressure.

D. Use of Caps Containing Solid Phase Support to Remove Unreacted Reactant from Reaction Wells:

After allowing sufficient time for completion of the reaction, a disposable plate bearing caps positioned to fit into the reaction vessels is moved into position and inserted into the reaction vessels. Each cap is a "barrier" enclosing a solid phase support bearing a binding agent for unreacted reactant. The caps are permeable to the liquid in the reaction vessel. After sufficient time and agitation for equilibration of binding, the caps are raised above the solvent level, and solvent and unbound material remaining in the caps is drained and/or rinsed back into the corresponding reaction vessel. The cap plate is then removed, and the reaction wells are prepared for the next step of synthesis.

E. Use of Caps Containing a Solid Phase Support to Retain Desired Products in the Reaction Wells.

Addition of reactants and reaction conditions are as described in section A. After allowing sufficient time for completion of the reaction, a disposable plate bearing caps that fit into the reaction vessels is moved into position and inserted into the reaction vessels. The caps are permeable to the liquid contained in the reaction vessel and contain a solid phase support, matched to the reaction step, that binds to the desired product. After sufficient time and agitation for equilibration of binding, unbound material is rinsed off the solid phase support. Conditions are then changed to release the desired product from the matrix. These changes may include, e.g., changes in the pH, hydrophobicity, ion concentration, temperature. After sufficient time and agitation for release of the product, the caps are moved above the solvent level, and solvent and released material are drained and/or rinsed back into the reaction vessel. The cap plate is then removed, and the reaction wells are prepared for the next step of synthesis.

F. Use of Caps Containing a Solid Phase Support to Introduce a Reactant or Catalyst to a Chemical Reaction.

Following the reaction, a solid phase bound catalyst may be removed and reused.

If the solid phase support contains a reactant, the product can be released from the solid support by appropriate treatment. Once the solid phase support has been removed from solution, a second solid phase support may be used to separate unreacted reactants from desired product, if desired. Furthermore, one solid phase support may contain more than one catalyst.

The following example relating to the present invention should not, of course, be construed as specifically limiting the invention, and such variations of the invention, now known or later developed, which would be within the purview of one skilled in this art, are to be considered to fall within the scope of this invention as claimed below.

EXAMPLE

As example of the use of this method for the synthesis of a combinatorial library follows. This library is synthesized using the reaction steps described by Boger, U.S. application Ser. No. 08/281,196 filed Jul. 26, 1994, hereby incorporated by reference. One example of such a synthesis is shown in Figure I. The Diels-Alder derived multifunctional scaffold molecule shown in Structure 4 contains three points of diversification in the synthesized library of compounds, at positions $R_1$, $R_2$, and $R_3$. In this example, the diacid shown in Structure 1 forms the scaffold group to which $R_1$, $R_2$, and $R_3$ will be attached. The BOC group refers to a t-butoxycarbonyl protecting group. There a re three sets of variants at the $R_1$, $R_2$, and $R_3$ groups, which are attached to the template in a series of three coupling steps. In the first two coupling reactions, variation is introduced by using various amines ($R_1$ and $R_2$), follow ed by one step where the variation is introduced by using a variety of carboxylic acid compounds ($R_3$). In the specific example here, 10 different amines are used at $R_1$, 10 different amines at $R_2$ and 8 different acids at $R_3$ (listed in Table 1 below). This will yield a 10×10×8 =800 component combinatorial library.

TABLE 1

Reactants used in the generation of a library containing multifunctional scaffold compounds.

| $R_1$ | | $R_2$ | | $R_3$ | |
|---|---|---|---|---|---|
| $A_1$ | Butyl amine | $A_2$ | Glycine methyl ester | $A_3$ | Benzoic |
| $B_1$ | Octyl amine | $B_2$ | p-Nitro benzyl-amine | $B_3$ | 4-hydroxyphenyl acetic acid |
| $C_1$ | 4-Methyl-benzylamine | $C_2$ | Methyl amine | $C_3$ | 3-Indole acetic acid |
| $D_1$ | Cyclohexyl-amine | $D_2$ | Benzylamine | $D_3$ | 2-Indole carboxylic acid |
| $E_1$ | Glycine methyl ester | $E_2$ | m-Methylbenzyl-amine | $E_3$ | Carbobenzoxy-glycine |
| $F_1$ | 2-Phenyl-ethylamine | $F_2$ | p-Methoxybenzyl-amine | $F_{34}$ | 3-Bromoprop-ionic |
| $G_1$ | 6-Aminocapro-nitrile | $G_2$ | Piperidine | $G_3$ | Hydrocinnamic |
| $H_1$ | Allyl amine | $H_2$ | Pyrrolidine | $H_3$ | trans-cinnamic acid |
| $I_1$ | Dibenzylamine | $I_2$ | Diethylamine | | |
| $J_1$ | Alanine methyl ester | $J_2$ | Morpholine | | |

The library will be coded as follows: $A_1A_2A_3$, $A_1A_2B_3$, $A_1A_2C_3$, $A_1A_2D_3$, $A_1A_2E_3$ ... $J_1J_2H_3$
Procedure The diacid (denoted HOOCRCOOH) (1.60 g, 5.14 mmol) is dissolved in 50 mL of dimethylformamide (DMF) and 5 mL of the solution is introduced to each of 10 sets of reaction vessels. N-Ethyl-$N^1$-dimethylaminopropyl carbodiimide (1.1 equivalents, introduced in a 150 mg/mL solution in sets of DMF) (EDCI) is added and the reaction is stirred at 25° C. for 15 minutes before the addition of 1 equivalent of each of the amines representing $R_1$ dissolved in DMF). One amine, each corresponding to one of the compounds $A_1$ to $J_1$, is added to each of the ten sets of reaction vessels such that ten unique reactions are conducted simultaneously. The reactions are stirred at 25° C. for 20 h before being introduced into the workup station. Alternatively, workup can occur in situ, for example if the cap method is being used. 5 mL of a 50% aqueous buffer solution in methanol adjusted to a pH at which the amines and N-acyl urea will be protonated, such as pH 5, is added to each reaction and the mixture is exposed to sufficient quantity of a cation exchange "AG-50W-X" resin to remove the unreacted amine, EDCI and the N-acyl urea. The unbound material is extracted with ethyl acetate, dried by passing through a cartridge of $MgSO_4$, and concentrated to leave the pure monoamides $HO(O)CRC(O)A_1$ to $HO(O)CRC(O)J_1$ (Structure 2).

Each of the monoamides, $RC(O)A_1$-$RC(O)J_1$, is dissolved in 20 mL of DMF. Aliquots (2 mL) are transferred to each set of the ten reactions vessels. EDCI (3eq, (2 mL, 150 mg/mL solution) is added followed by amines (Variant II, $A_2$ to $J_2$, 3 equivalents of stock solution in DMF) in a manner such that 100 unique reactions are conducted simultaneously. The reactions are stirred at 25° C. for 20 h before being introduced into the workup station, or before caps containing appropriate resins are introduced. Buffer methanol solution (pH 5, 4 mL) is added to each reaction and the solutions are allowed to interact with "AG-501-X8" to remove the unreacted amine, EDCI and N-acyl urea. The effluent is extracted with ethylacetate, dried through $MgSO_4$ and concentrated to yield the pure diamides ($A_1(O)CRC(O)$ $A_2$, $A_1(O)$ $CRC(O)B_2$, $A_1(O)$ $CRC(O)J_2$ ... $A_2(O)CRC(O)$ $J_2$) (Structure 3).

The resulting 100 diamides are dissolved in 4M HCl/ethylacetate) (4 mL) and aliquots (0.5 mL) are pumped into each of the 8 reaction chambers (800 total). The reactions are stirred for 30 min at 25° C. and the solvent is evaporated from each chamber to leave the crude amine hydrochloride salts. DMF (0.5 mL) is added to each vessel to dissolve the samples and EDCI (0.4 mL, 150 mg/mL solution) followed by the set of acids for position $R_3$ (Variant III, $A_3$-$H_3$, 2 eq, in DMF solution) are introduced in a manner such that 800 unique reactions are conducted simultaneously. The reactions are stirred at 25° C. for 20 hours before transferring to the workup station or being allowed to interact with the resin in situ. Buffer solution (pH 6, 0.7 mL) is added to each and the reaction is passed through a mixed bed resin such as "AG-501-X8". The effluent is extracted with ethylacetate, dried and concentrated to yield the 800 compounds containing $A_1A_2A_3$-$J_1J_2H_3$ of the combinatorial library (Structure 4).

All patents and publications mentioned in this specification are indicative of the levels of those skilled in the art to which the invention pertains. All patents and publications are herein incorporated by reference to the same extent as if each individual publication is specifically and individually indicated to be incorporated by reference.

Other embodiments are within the following claims. Thus while several embodiments have been shown and described, various modifications may be made to the invention disclosed herein, without departing from the spirit and scope of the present invention.

I claim:

1. A method of inverse solid phase synthesis comprising the steps of:

(a) reacting at least two reactants in a solution to obtain a product; and (b) removing at least one unreacted said reactants with a solid phase matrix wherein said solid phase matrix covalently binds said at least one unreacted said reactants, leaving substantially all of said product in said solution.

2. A method of inverse solid phase synthesis comprising the steps of:

(a) reacting at least two reactants in a solution to obtain a product; and (b) removing at least one unreacted said reactants with a solid phase matrix, leaving substantially all of said product in said solution;

(c) reacting said first product with an additional reactant in a solution to obtain a second product;

(d) removing unreacted said additional reactant with a solid phase matrix, leaving substantially all of said second product in said solution; and (e) repeating steps (c) and (d) n times, wherein n is 1 to 50.

3. The method of claim 1 wherein at least one of said at least two reactants is an amine.

4. The method of claim 3 wherein at least one of said at least two reactants is selected from the group consisting of: butyl amine, octyl amine, 4-methylbenzylamine, cyclohexylamine, glycine methyl ester, 2-phenylethylamine, 6-aminocapronitrile, allyl amine, dibenzylamine, and alanine methyl ester.

5. The method of claim 2 wherein said additional reactant is an amine, and said solid phase matrix is a cation exchange resin.

6. The method of claim 5 wherein said additional reactant is selected from the group consisting of glycine methyl ester, p-nitrobenzylamine, methyl amine, benzylamine, m-methylbenzylamine, p-methyoxybenzylamine, piperidine, pyrrolidine, diethylamine, morpholine and said solid phase matrix is a cation exchange "AG-50W-X" resin.

7. The method of claim 2 wherein said reaction of at least two reactants in solution to form a product is a Diels-Alder reaction.

8. The method of claim 2 wherein said step of reacting said first product with an additional reactant is a Diels-Alder reaction.

9. The method of claim 2 wherein one of said repeated steps is a Diels-Alder reaction.

10. The method of claim 2 wherein at least one of said at least two reactants is an amine, and said solid phase matrix is a cation exchange resin.

11. The method of claim 10 wherein at least one of said at least two reactants is selected from the group consisting of: butyl amine, octyl amine, 4-methylbenzylamine, cyclohexylamine, glycine methyl ester, 2-phenylethylamine, 6-aminocapronitrile, allyl amine, dibenzylamine, and alanine methyl ester and said solid phase matrix is a cation exchange "AG-50W-X" resin.

* * * * *